(12) United States Patent
Desai et al.

(10) Patent No.: US 10,488,384 B2
(45) Date of Patent: Nov. 26, 2019

(54) SYSTEM AND METHOD FOR ASSESSING POWER TRANSFORMERS

(71) Applicant: Electric Power Research Institute, Inc., Charlotte, NC (US)

(72) Inventors: Bhavin N. Desai, Concord, NC (US); Timothy Raymond, Schuylerville, NY (US)

(73) Assignee: ELECTRIC POWER RESEARCH INSTITUTE, INC., Charlotte, NC (US)

( * ) Notice: Subject to any disclaimer, the term of this patent is extended or adjusted under 35 U.S.C. 154(b) by 1131 days.

(21) Appl. No.: 14/534,593

(22) Filed: Nov. 6, 2014

(65) Prior Publication Data

US 2015/0127277 A1 May 7, 2015

Related U.S. Application Data

(60) Provisional application No. 61/900,642, filed on Nov. 6, 2013.

(51) Int. Cl.
*G01R 31/40* (2014.01)
*G01N 25/00* (2006.01)
*G01N 33/26* (2006.01)
*G01R 31/02* (2006.01)
*G01N 33/28* (2006.01)

(52) U.S. Cl.
CPC ......... *G01N 33/26* (2013.01); *G01N 33/2841* (2013.01); *G01R 31/027* (2013.01)

(58) Field of Classification Search
CPC ... G01N 33/26; G01N 33/2841; G01R 31/027

USPC ......... 720/58, 127, 70, 73, 75, 77; 700/295, 700/291, 297
See application file for complete search history.

(56) References Cited

U.S. PATENT DOCUMENTS

| 8,361,351 | B2 * | 1/2013 | Rapp | C09K 5/10 |
| | | | | 174/17 LF |
| 2004/0249777 | A1 * | 12/2004 | Ransing | G06F 19/3437 |
| | | | | 706/45 |
| 2009/0312881 | A1 * | 12/2009 | Venturini Cheim | G01D 4/004 |
| | | | | 700/292 |
| 2012/0317058 | A1 * | 12/2012 | Abhulimen | G06N 99/005 |
| | | | | 706/2 |
| 2013/0076130 | A1 * | 3/2013 | Zhang | H02J 3/16 |
| | | | | 307/17 |
| 2013/0138384 | A1 * | 5/2013 | Kong | B01D 63/087 |
| | | | | 702/128 |
| 2014/0222355 | A1 | 7/2014 | Cheim et al. | |

* cited by examiner

*Primary Examiner* — Mohamed Charioui
*Assistant Examiner* — Jeremy Delozier
(74) *Attorney, Agent, or Firm* — Trego, Hines & Ladenheim, PLLC; Brando Trego; Jonathan Hines

(57) ABSTRACT

A system and method for evaluating power transformers is disclosed. The method includes the steps of acquiring data representing one or more parameters of a power transformer, using rules to derive one or more broad physical conditions of the power transformer from the acquired data, and using the broad physical conditions as inputs to compute a plurality of indices. Each index represents a category of failure mechanisms of the power transformer. The method further includes the steps of using the plurality of indices to determine a corrective action and performing the corrective action on the power transformer.

16 Claims, 11 Drawing Sheets

SYSTEM AND METHOD FOR ASSESSING POWER TRANSFORMERS

BACKGROUND OF THE INVENTION

The field of power transformer diagnostics is characterized by inexact reasoning and reasoning under uncertainty. Lack of information on the construction and design of a transformer, limited test opportunities, uncertain operating conditions and a lack of empirical data combine for a task that is far from an exact science. Interpretation of test results is more of an art than a science. Practitioners must examine sparse evidence from a variety of sources and make an educated guess as to the presence of a potential fault condition, the severity of that fault condition and the appropriate corrective action (which often is limited to costly replacement).

Unfortunately, in today's industry environment, these same activities must be performed with reduced manpower, reduced domain expertise and an ever increasing amount of raw data. In addition, asset management and maintenance decision are coming under increased scrutiny, both from within the company as pressures to constrain costs mount, and from external regulators. Transformers are a key component in power delivery. Transformer failures can cost millions of dollars in consequential costs besides leading to other system reliability and operational challenges.

Accordingly, there is a clear need for an established, defensible, transparent and repeatable condition assessment methodology.

BRIEF SUMMARY OF THE INVENTION

These and other shortcomings of the prior art are addressed by the present invention, which provides an improved diagnosis and better understanding of transformer condition to allow for operation and maintenance decisions and replacement decisions with a holistic methodology that utilize sophisticated algorithms based on the knowledge of transformer design, construction and failure mechanisms. The methodology enables a consistent, systematic, repeatable and documented process.

According to one aspect of the present invention, a method for evaluating and diagnosing a condition of a power transformer contained in a power transmission system includes the steps of acquiring data representing one or more parameters of a power transformer, using rules to derive one or more broad physical conditions of the power transformer from the acquired data, and using the broad physical conditions as inputs to compute a plurality of indices. Each index represents a category of failure mechanisms of the power transformer. The method further including the steps of using the plurality of indices to determine a corrective action, and performing the corrective action on the power transformer.

According to another aspect of the present invention, a system configured to evaluate and diagnose a condition of a power transformer contained in a power transmission system includes a computing device configured to provide a user interface to allow a user to input data and execute rules to analyze the data, and a plurality of modules executed by the computing device, the modules being configured to conduct various stages of analysis on one or more power transformers. The modules include an input module executed by the computing device to allow a user to input data gathered for each power transformer being analyzed, an analysis engine module executed by the computing device in response to the data being entered into the system, the analysis engine executing pre-defined rules to determine indices, and an output module executed by the computing device in response to the analysis engine module determining indices. The output module displays results of the analysis engine module for a user to view and prompts the user to perform an action representative of a value assigned to the indices.

BRIEF DESCRIPTION OF THE DRAWINGS

The subject matter that is regarded as the invention may be best understood by reference to the following description taken in conjunction with the accompanying drawing figures in which.

DETAILED DESCRIPTION OF THE INVENTION

Figure 1:
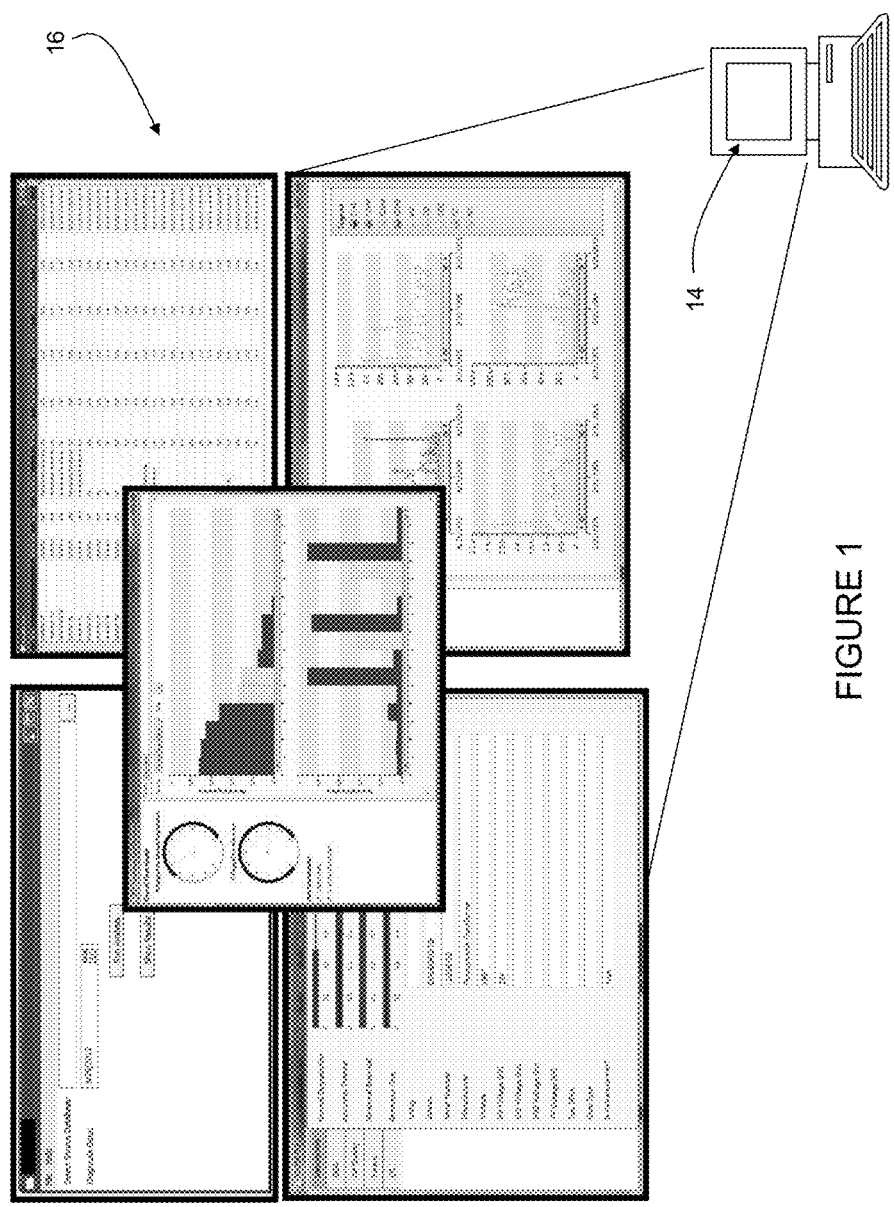
FIG. 1 is a screen shot of a graphical user interface of the system according to an embodiment of the invention.
Figure 2:
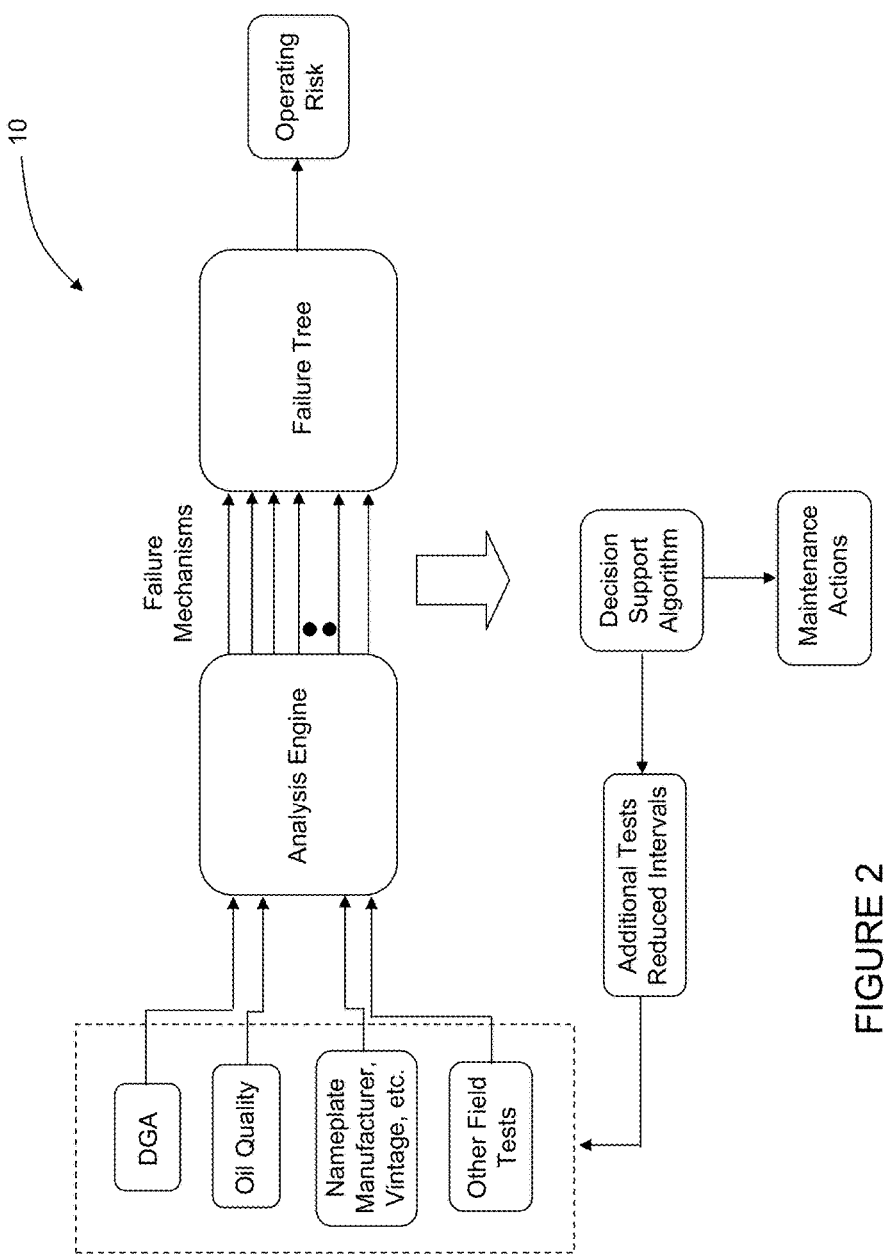
FIGS. 2-6 are flow charts of the system and method according to an embodiment of the invention.
Figure 3:
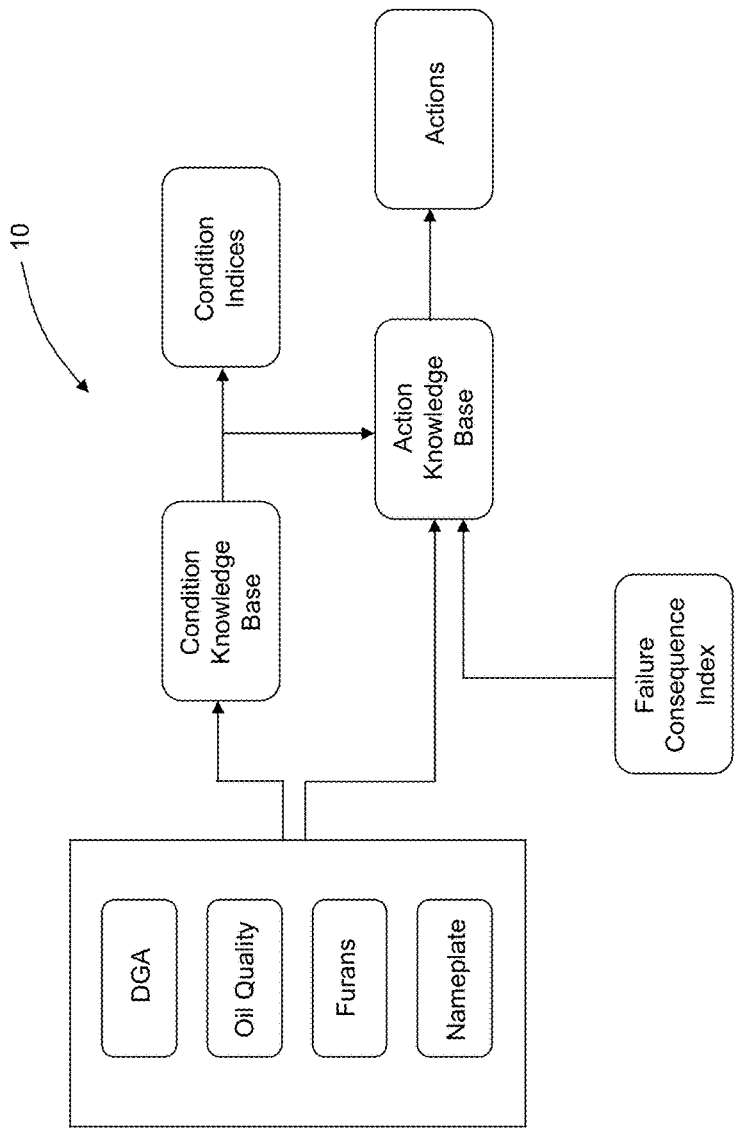

A system and method according to an embodiment of the invention is shown generally in FIGS. 1-6 at reference numeral 10. The system and method uses hardware and software to provide a rule-based expert system capable of performing transformer diagnosis. One example of a rule-based expert system is MYCIN. MYCIN is a rule-based inference engine developed by Stanford University for the medical field to evaluate hypothesis. In the case of transformer diagnostics, the hypotheses that are to be evaluated are whether a given failure mode or failure mechanism is present. Evidence, in the form of test data and nameplate information, is evaluated by rules to determine a "belief" that a given failure mechanism is present.

For purposes of this discussion, the system and method of the current invention will be discussed with respect to the MYCIN rule-based inference engine; however, it should be appreciated that the current invention is not limited to MYCIN and may be based off of other suitable platforms.

Before discussing the current invention in detail, it is important to provide a general understanding of rule-based expert systems such as MYCIN. To overcome some of the perceived limitations of a rigorous probabilistic analysis, the designers of the MYCIN system proposed an approach that allows the domain expert, providing the knowledge, to express uncertainty in a natural fashion without the restrictions of rigorous probability theory. Central to this approach was the quantitative expression of confirmation (or alternatively disconfirmation). Confirmation could be defined as the degree to which a piece of evidence confirms a hypothesis. Confirmation differs from probability in some key aspects. Foremost is the notion that confirmation in a hypothesis does not necessarily disconfirm the negation of the hypothesis. In other words, confirmation and disconfirmation are separate and must be dealt with differently.

To address this, MYCIN introduced two new quantities, termed belief (MB) and disbelief (MD). MB[h,e] is the measure of increased belief in the hypothesis, h, based on the evidence, e. MD[h,e] is the measure of decreased belief in the hypothesis, h, based on the evidence, e. These quantities are expressed as numbers in the range 0 to 1, with higher values indicating greater degree of belief or disbelief. Values equal to 1.0 express certain belief or disbelief in a hypothesis. These functions are not to be treated as probabilities, but can be expressed in terms of probability as follows:

$$MB[h, e] = \begin{cases} 1 & \text{if } P(h) = 1 \\ \frac{\max[P(h \mid e), P(h)] - P(h)}{1 - P(h)} & \text{otherwise} \end{cases} \quad (1.1)$$

$$MD[h, e] = \begin{cases} 1 & \text{if } P(h) = 0 \\ \frac{\min[P(h \mid e), P(h)] - P(h)}{-P(h)} & \text{otherwise} \end{cases} \quad (1.1)$$

From the above, it is possible to see that, although different than probability, the measures of belief and disbelief do have some mathematical foundation. The measure of belief is approximately equal to the conditional probability in instances where there are a large number of mutually exclusive possibilities (small prior probability P(h)).

For the sake of convenience, a third quantity, referred to as the "certainty factor", was developed to provide a convenient way to express the combined measures of belief and disbelief. Originally, the certainty factor was simply the difference between the total measure of belief and disbelief (MB-MD). However, this led to some difficulties in certain scenarios. To resolve these problems, the certainty factor was re-defined as follows:

$$CF = \frac{MB - MD}{1 - \min(MB, MD)} \quad (1.2)$$

With this redefinition, it is possible to drop the notion of belief and disbelief when convenient and focus on the certainty factor as the central measure of belief. However, this is only advantageous in simplifying computations and reducing data storage requirements. In developing the knowledge base, there is some conceptual benefit to maintain a distinction between belief and disbelief. Some of the key characteristics of the certainty factor are given in the table below.

| Characteristics | Values |
| --- | --- |
| Ranges | $0 \le MB \le 1$ |
| | $0 \le MD \le 1$ |
| | $-1 \le CF \le 1$ |
| Certain True Hypothesis | MB = 1 |
| P(H\|E) = 1 | MD = 0 |
| | CF = 1 |
| Certain False Hypothesis | MB = 0 |
| P(H'\|E) = 1 | MD = 1 |
| | CF = -1 |
| Lack of Evidence | MB = 0 |
| P(H\|E) = P(H) | MD = 0 |
| | CF = 0 |

When interpreting certainty factors, it is critical to keep in mind that certainty factors are not probabilities. Aside from the obvious observation that beliefs range from −1 to +1, where probabilities typically range from 0 to 1, there are some minor, subtle differences. For example, take a set of four mutually exclusive and exhaustive outcomes, where one and only one outcome can be true. In the absence of any information, Bayesian probability might assign an equal probability to each of 0.25, or perhaps allocate some statistically-based prior probabilities that total 1.0. However, the certainty factor or belief for each outcome would, by the definition of a certainty factor, be zero since there is no evidence to support a higher or lower belief. Whereas in traditional probability theory, the sum of the probabilities for the set of all possibilities must equal 1, this restriction is not present in certainty factor theory.

Another significant difference between probability theory and certainty factors concerns the negation of a hypothesis. In traditional probability theory, the probability of the negation of a hypothesis is equal to one minus the probability of the hypothesis, ie. P(¬h)=1−P(h). In certainty factor theory, however, this is not true. The certainty factor in the negation of a hypothesis is equal to the negative of the certainty factor in a hypothesis, ie. CF(¬h)=−CF(h). In terms of the present discussion, if there is a +0.2 belief in "lead heating" being present, then there is a −0.2 belief in "lead heating" NOT being present.

Having developed a suitable means for expressing belief and disbelief in a hypothesis given a single piece of evidence, there must be a means for combining the beliefs contributed by multiple pieces of evidence to arrive at a representative belief in a given hypothesis or conclusion. This combining function should obey several properties. First, it should be independent of order, ie. A⊕(B⊕C)=(A⊕B)⊕C. In addition, the combining function should follow the logic of the certainty factors. If two indicators support a given hypothesis, the combined belief in that hypothesis should be higher than the belief from each indicator taken individually. Similarly, if two beliefs support the negation of a hypothesis (e.g. that a given alternative is not attractive), then the combined belief should be more negative than each individual belief. Finally, in the case of conflicting, the combined belief should be closer to 0, or "unknown".

The summation method utilized in the MYCIN program has all of the properties outlined above. This summation method, here called the "MYCIN Sum", is a mathematical expression of the idea that two beliefs with the same conclusion will reinforce each other, while opposite beliefs will reduce certainty (move the certainty factor toward 0) in a certain outcome.

$$CF_{COMBINE}(X, Y) = \begin{cases} X + Y(1 - X) & X, Y \text{ both} > 0 \\ \frac{X + Y}{1 - \min(|X|, |Y|)} & \text{one of } X, Y < 0 \\ X + Y(1 + X) & X, Y \text{ both} < 0 \end{cases} \quad (1.3)$$

When combining beliefs, if both beliefs are consistent, they will reinforce the combined belief in a given conclusion. For example, if there are two test results that both suggest a given transformer might be "aged", then there is greater confidence that the unit is in fact aged. However, if one test suggests an aged transformer and another suggests a serviceable transformer, then the combination of the two leaves the practitioner with an increased level of uncertainty.

The key advantage of certainty factors is that they allow the consideration of multiple pieces of evidence without needing large numbers of prior or conditional probabilities. In an oversimplified respect, certainty factors assume all evidence is conditionally independent, and can therefore be represented simply as a series of rules independent of order.

Whereas Bayesian belief networks or other more mathematically rigorous methods require more structure than simple rules allow, MYCIN certainty factors allow for a rule-based system that can be developed in an evolutionary process, with each rule encapsulating a single "nugget" of knowledge, versus other systems where structure and ontology must be carefully designed in a fully premeditated manner.

Referring to FIGS. 1-6, in general, the system 10 includes software disposed on computer readable media and a computing device or processor 14 to process data and perform pre-determined functions. The software provides an input module 11, an analysis engine module 12, an output module 13, and a graphical user interface (GUI) 16 to allow a user to access the input module 11 and allow a user to input data representative of a particular transformer, such as name plate information, inspection data, etc. The analysis engine module 12 (described in more detail below) uses the processor 14 and pre-programmed expert rules to analyze the data, and the output module 13 provides a user with results from the analysis engine module 12 so that the user can take an appropriate action. It should be appreciated that the method may be performed without the hardware and software.

Examples of input data include:

Components—Components are the top-level objects. They represent the physical systems or subsystems being diagnosed. The most obvious component is the "Transformer" component. Components can contain subcomponents, e.g. bushings or load tap changers. Components are also the containers for information, in the form of Activities. At a high level, containers also contain Facts in the form of Failure Mechanisms or Actions (see section on Facts)

Activities—Facts are generally organized into Activities, with the exception of unique component level facts, such as Failure Mechanisms and Actions. An Activity acts as a template of facts at a given instance in time. There may be several historical instances of activities in a given "history", from which trends are generated. In addition, a rule-based diagnosis is performed at each historical activity instance (point-in-time). Each component also has associated with it a Description Activity (only one instance) that provides facts that describe the component. These are basic facts like "Manufacturer" or "HV Voltage" that do not change with time.

Facts—A fact is a kernel of knowledge or a single piece of factual information that can be used by the inference engine rules to reason about other facts. Some of the facts are "input facts" as given by the user. Other facts are inferred from the rules. There are several fact types that include:

Text facts—Facts representing a string

Numeric facts—Facts representing numeric values, generally continuous

List facts—Facts that can take on a discrete number of known values (e.g. Manufacturer). A value is also included for "Unknown", where the given value is unknown in the rule base.

Boolean Facts—A fact that takes on a Boolean yes/no or true/false value. This is the most generic type of fact Failure mechanism—An extension of a Boolean Fact that indicates whether a given failure mechanism is present (true or yes). This fact type is generally placed at the component level.

Action—Also an extension of a Boolean Fact that indicates whether a given Action should be undertaken (true or yes). This fact type is also generally placed at the component level.

Figure 8:
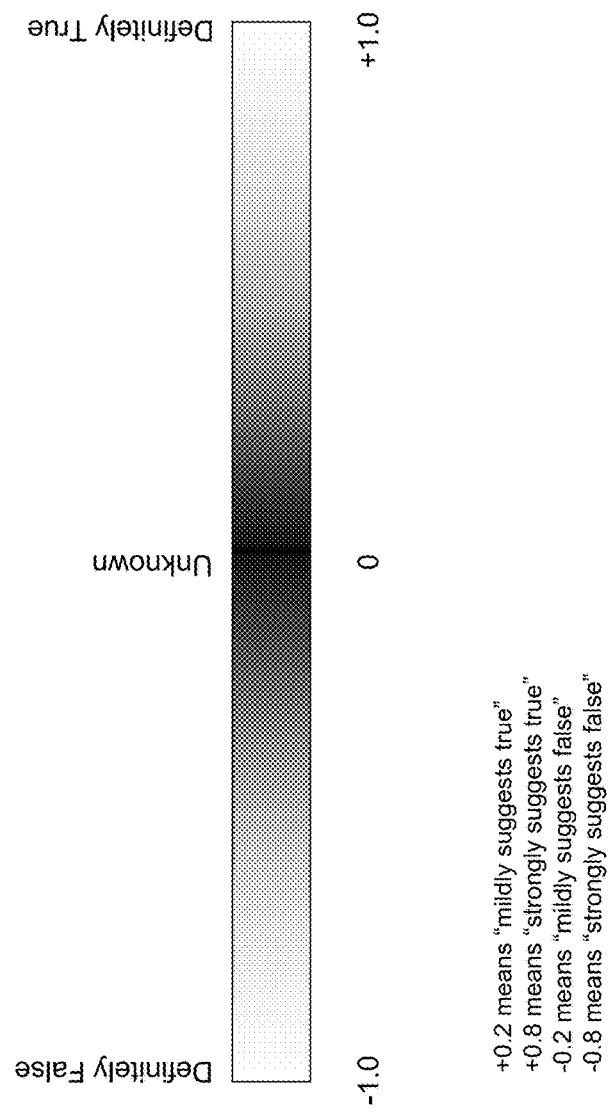
FIG. 8 is a graphical representation of a belief according to the system and method of the current invention.

Each fact, along with a discrete answer, has associated with it a Belief, i.e., a number between −1.0 and +1.0, see FIG. 8, that indicates the certainty one has in the value of the fact. It is used in the rules to determine the weight a given fact has in the evaluation of that rule.

The analysis engine module evaluates rules, as outlined above. At each evaluation point, the analysis engine module iterates through all of the rules for the given component and evaluates each rule at that point in the component history. Rules follow a specific format and are expressed in a human-readable text format with a defined lexicon.

The rules are structured with two parts, a premise (If-part) and a conclusion (Then-part) and alternative (Else-part). As with all rule-based expert systems, the premise is first evaluated. If the premise evaluates to true (a certainty factor greater than a nominal threshold), then the conclusion is "fired" or executed. A certainty factor can be assigned to both the premise and the conclusion. The total certainty factor for the rule is the product of the premise and the conclusion.

By way of illustration, below is a typical rule:

```
IF Transformer.DGA.Ethylene = HIGH (50, 250) THEN
Transformer.DGA.blfHighTemp (0.4) ELSE
!Transformer.DGA.blfHighTemperature
(0.2) END
    "IF Ethylene is High THEN
        there is high temperature heating (T3) with a certainty factor
        (CF) of 0.4
    ELSE
        there is NOT high temperature heating (T3) with a certainty
        factor (CF)
    of 0.2)."
```

The premise "Ethylene is high" can be assigned a certainty factor to express the observer's confidence that the level of Ethylene is indeed "high". For example, based on the value of Ethylene, the observer might assign a belief of 0.6 that Ethylene is "high". When a certainty factor is assigned to the premise, this is referred to as the "tally". The certainty factor given in the conclusion of the rule represents the full amount of belief that would be assigned to the hypothesis if the premise were certain (tally equal to 1.0).

When the premise is a Boolean value, as is the case when observations or facts have a yes/no value or are a discrete list of possibilities, a separate certainty factor for the premise might seem unnecessary. However, when the indicator is numeric or is defined by a continuous range rather than discrete values, the value of the indicator bears some relation to the strength of the indication. The "tally" is a useful mechanism for relating the strength of the indication to the conclusion of the rule (diagnosis or hypothesis).

In the case of numeric indicators, the numeric value of the indicator is assigned a certainty factor via the use of some function. This function can take any form, but presently consists of a simple sigmoid function between "good" and "bad" thresholds. As an example, consider the indicator "Ethylene". If the hypothesis being evaluated is "high temperature heating (T3)", then a higher Ethylene content would support this hypothesis. Rather than defining a single threshold value for Ethylene, where all Ethylene concentrations below the threshold are assumed to be "good" (belief of −1.0) and those above are "bad" (belief of +1.0), a function can be defined.

The S-Function for HIGH is defined as:

$$\begin{cases} -1, x \le \alpha \\ 1 - 4\left(\frac{x-\alpha}{\gamma-\alpha}\right)^2, \alpha < x \le \beta \\ -1 + 4\left(\frac{x-\gamma}{\gamma-\alpha}\right)^2, \beta < x \le \gamma \\ 1, x > \gamma. \end{cases}$$

To reduce inputs, beta defaults to alpha+gamma/2. This is purely for convenience. The LOW function is simply the negation of the HIGH function, such that increasing values of the underlying numeric fact value decrease the belief that the value is LOW. A third function, MODERATE, is also defined to allow for interpretation of values that may have diagnostic value over a range, but not above or below it.

The conclusion of a rule only is applied, or "fires", when the belief in the premise exceeds a given threshold. In the case of negative beliefs, the rule would not generally fire. In the example rule above, however, a second conclusion was given as part of an "else" clause. The "else" clause allows the expression of disconfirming evidence, in this case low values of Ethylene. Recall that belief and disbelief are conceptually two different actions. Therefore, rules disconfirming a hypothesis should be made explicit.

The premise of the rules may contain certain elementary logical expression such as "And", "Or" and "Not". These logical operations are defined as shown in the table below. Note that the logical combination of evidence in the premise is a different activity than the combination of distinct, independent rules.

| Expression | Definition |
| --- | --- |
| $E_1$ AND $E_2$ | $\min[CF(H|E_1), CF(H|E_2)]$ |
| $E_1$ OR $E_2$ | $\max[CF(H|E_1), CF(H|E_2)]$ |
| NOT $E_1$ | $-CF(H|E_1)$ |

While the appeal of the system is the independent nature of the individual rules, allowing for the easy addition of knowledge, there are some restrictions that should be followed to maintain a coherent rule set:
1. Given mutually exclusive hypotheses for an observation, the sum of their certainty factors (CFs) should not exceed 1.
2. Dependent pieces of evidence should be grouped into single rather than multiple rules.
3. Care must be taken to avoid conflicting rules, i.e., a rule that states a hypothesis is definitely true and a rule that states the same hypothesis is definitely false. Absolute certainty in rules must be used carefully.

In the case of a decision support system for transformer diagnostics, the hypotheses that are to be evaluated are whether a given failure mode or failure mechanism is present. Evidence, in the form of test data and nameplate information, is evaluated by rules such as those described above to determine a "belief" that a given failure mechanism is present.

The general overall evaluation process is as follows:
Diagnose subcomponents
Compile list of historical activity dates to serve as discrete assessment points
For each date in the list above:
For each rule in the component rule base
Evaluate Rule Predicate
If Rule Predicate is greater than threshold, "fire" rule
If Rule is an Assignment Rule:
process fact assignment assigning a Belief to the assigned facts equal to the Rule Predicate Belief.
Else:
If Rule Predicate Belief is above rule "fire" threshold:
Process True Belief Assignment List
Else If Rule Predicate Belief is below rule "fire" threshold:
Process False Belief Assignment List
State Mechanism Beliefs
Evaluate Normal Degradation Increment
Compute Normal Degradation Index There can be any number of failure mechanisms, arranged in any fashion that makes physical sense. New failure mechanisms can be added to the rule base at any time, without the need to adjust prior rules. Failure mechanisms can be as broad as "thermal" or as fine-grained as "winding insulation deterioration—thermal degradation". Fine-grained classifications provide more information to the user, but require more rules (and more evidence) to differentiate between the individual failure mechanisms. The underlying diagnostic method must also be capable of differentiating between possible failure mechanisms.

In addition to failure mechanisms, the system approach can be applied to other "hypotheses", such as whether or not a given action should be performed. The rule-based approach allows additional hypotheses to be added to the knowledge base simply by adding additional rules. In this fashion, a series of actions or decisions can be assessed to give users guidance on possible maintenance or testing that should be performed given the available information. For example, a rule might be defined to suggest oil reclamation or replacement if the oil quality drops below thresholds. As another example, a rule could be defined that would suggest power factor testing if moisture-in-oil indicates the possibility of high moisture.

These hypotheses need not be limited to routine maintenance or testing, either. A hypothesis could be defined along the lines of "This transformer should be replaced" and rules added to apply various pieces of information or evidence that may favor or disfavor this hypothesis.

There are, however, a couple of caveats. First, the assessment is only as good as the information provided by the user and the expert knowledge. For example, if the rules do not consider transformer cost or criticality in a replacement decision, then obviously the resulting belief would not account for these factors. (As an aside, this highlights the need for a transparent rule base.) In addition, the belief or certainty factor only indicates the amount of evidence supporting a replacement decision, not remaining service life. In assessing decisions in this fashion, there is a significant disadvantage in that the utility considerations are not explicit, but are buried in the certainty factors.

Before discussing the system and method approaches in detail, it is appropriate to first discuss some of the desired characteristics and requirements for a successful transformer fleet decision support system. These requirements shall guide the selection of the assessment methodologies.

Operate with a minimum of data: With the advancing age of most transformer fleets, the utilization of this readily available data in making asset management decisions based on unit condition is essential. However, the amount of data involved is quite significant. Dissolved Gas Analysis (DGA)

data alone can account for tens of thousands of test records for fleets as small as one hundred units. The use of an expert system provides an efficient means for analyzing the readily available data in order to distinguish units that may be candidates for additional testing and investigation. The asset manager's field of view can then be shifted from the large fleet to a small subset of suspect units.

Example rules for dissolved gas analysis (DGA) using the system are shown below. The numbers in the square brackets specify the "good" and "bad" limits respectively. For example, the term "H2 is High[100, 1000]" specifies a belief of −1.0 for H2 values less than 100 ppm, a +1.0 belief for H2 values above 1,000 ppm, and beliefs interpolated between −1.0 and +1.0 for H2 values between 100 and 1,000 ppm.

```
IF (H2 is High [100, 1000] AND NOT (CH4 is High [0, 400] OR C2H6 is
High [0, 200]
OR C2H4 is High [0, 150] OR C2H2 is High[0, 10])) THEN PD (1.0)
IF ((CH4 is High [0, 400] OR C2H6 is High [0, 200]) AND NOT (C2H4
is High [0, 150]
OR C2H2 is High [0, 10])) THEN T1-T2 (1.0)
IF (C2H4 is High [0, 150] AND NOT C2H2 is High [0, 10]) THEN
T2-T3 (1.0)
IF (C2H2 is High [0, 10] AND NOT (CH4 is High [0, 400] OR C2H6 is
High [0, 200]
OR C2H4 is High [0, 150])) THEN D1 (1.0)
IF (C2H2 is High [0, 10] AND (CH4 is High [0, 400] OR C2H6 is
High [0, 200] OR
C2H4 is High [0, 150])) THEN D2 (1.0)
```

In the expert system described herein, the minimum threshold for data was intentionally set quite low, requiring only DGA data and some limited nameplate data (vintage, manufacturer, MVA rating). Available data varies widely depending upon company maintenance philosophies and recordkeeping efforts. Most often, DGA and oil quality data is readily available in a convenient electronic format. Demographic information such as transformer manufacturer, vintage, voltage, MVA rating and cooling type are available to widely varying degrees. Electrical test data, such as insulation power factor or TTR, is generally less commonly available, particularly in a format amenable to automated processing. It is essential that a practical method for supporting power transformer maintenance and asset management decisions be capable of providing a useful result with a minimum amount of information. Obviously, some information must be present. Otherwise, the analysis would amount to random guessing. In order to provide a maximum of information with a minimum of effort, the practical minimum set of data shall consist of DGA test data. Ideally, some transformer nameplate information would also be included in this minimum set, but need not be strictly necessary.

Operate with missing data: Data quality and data set completeness varies from one company or population segment to the next. Even within relatively complete data sets, it is likely that some information will be missing or deemed erroneous. To be practical, the assessment methodology must not be impeded by missing data. The methodology must be capable of providing the best evaluation of the existing evidence without penalizing for missing data. This requirement is essential.

Allow modification of knowledge base as knowledge evolves: The problem domain of power transformer diagnostic is highly complex with surprisingly little supporting data. Asset owners and operators typically know very little about the specific design details of individual power transformers. Design details vary considerably with manufacturer, vintage and duty. Given the magnitude of the problem at hand, it is impractical, and inefficient, to develop a complete and comprehensive knowledge base. To do so would require a tremendous amount of effort and resources and ultimate success would not be guaranteed. Therefore, it is more practical to produce a knowledge base that covers the most common scenarios. As information or experience is gained, or unusual situations are encountered, the knowledge base should allow for the addition of new intelligence without requiring a complete refactoring of the knowledge base. Ideally, new knowledge could be captured is an isolated and modular fashion without requiring extensive modification of the current knowledge base. This would allow for the efficient development of an evolving knowledge base.

Transparent: In order to gain industry acceptance and provide maximum decision support, the assessment methodology should be transparent. The user should be able to gain an explanation for each conclusion produced by the tool in terms of the supplied evidence. Ideally, this explanation would be in something approximating natural language. However, it would be sufficient if users were able to trace through the assessment methodology in terms of the underlying mathematics and algorithm with sufficient detail to trace the reasoning behind each conclusion.

Enable support for a variety of decisions: This assessment methodology will be applied to a variety of decision-making tasks including, but certainly not limited to, replacement and asset management decisions or maintenance and monitoring tasks. Examples of the latter might include additional testing to narrow the range of possible diagnoses, increased surveillance of suspect units, or corrective maintenance of undesirable conditions.

Scalable to large amounts of data with varying frequency: As online monitoring devices are becoming more economical and gaining industry favor, the amount and frequency of available data is increasing. This additional information can provide a wealth of diagnostic insight, provided the assessment methodology can scale to handle the increased data bandwidth. Online DGA monitors are particularly intriguing. These devices are capable of detecting rapidly evolving failure modes. This detection capability is useless, however, unless there is some means to bring the potential fault to the attention of personnel in a position to intervene before catastrophic failure occurs.

A guiding principle in the development of the system and methodology is to limit the initial data requirements to data that is readily available in an electronic form convenient for automated analysis. The initial analysis is then used to target more costly data gathering or testing efforts. DGA and oil quality data is often available in a format that can be easily exported to a spreadsheet or database. Along with some basic nameplate information, it is that the initial screening analysis is done utilizing this readily available information.

The following is a detailed list of initial data requirements. The methodology is designed to be applicable using whatever data is available, as much as possible. This is one of the key requirements outlined above. As a minimum, DGA data is required, along with some minimal transformer information (items marked with a "1"). Additional information is strongly encouraged (items marked with a "2"). Other data will be utilized when available to refine the analysis.

Transformer Data:
Serial Number (1)
Manufacturer (1)
Year of Manufacture (1)

Oil Preservation System (2)
Transformer or Autotransformer
Core or Shell type
Temperature Rating (55 C, 65 C, 55/65 C)
Winding Voltages/Connections
MVA Ratings (2)
Cooling Mode Types (2)
Is there an LTC? (2)
Manufacturer
Model
Oil Preservation Type on LTC Compartment
Is there a DETC?
DGA Data (1):
Serial Number (or some other unique equipment identifier)
Sample Date
Compartment (if data includes LTC DGA or DGA from PST)
$H_2$
$CH_4$
$C_2H_6$
$C_2H_4$
$C_2H_2$
CO
$CO_2$
$O_2$
$N_2$
Oil Quality Data:
Serial Number
Sample Date
Oil Temperature during Sampling
Moisture
D1816
IFT
Acidity
Color
Furans Dissolved Gas Analysis (DGA) is one of the most useful and most widely used power transformer condition assessment techniques. This technique is sensitive to a wide range of malfunctions, both thermal and electrical, which could eventually lead to failure of a transformer if corrective measures are not taken.

Sampling intervals are typically from 1 to 3 years depending on the size and voltage of the transformer; with more frequent sampling for large, critical units and less frequent sampling for smaller, less critical units. On more critical units, or units exhibiting signs of a potential evolving fault, online gas monitors may be utilized that provide DGA measurements at frequent intervals.

Figure 7:
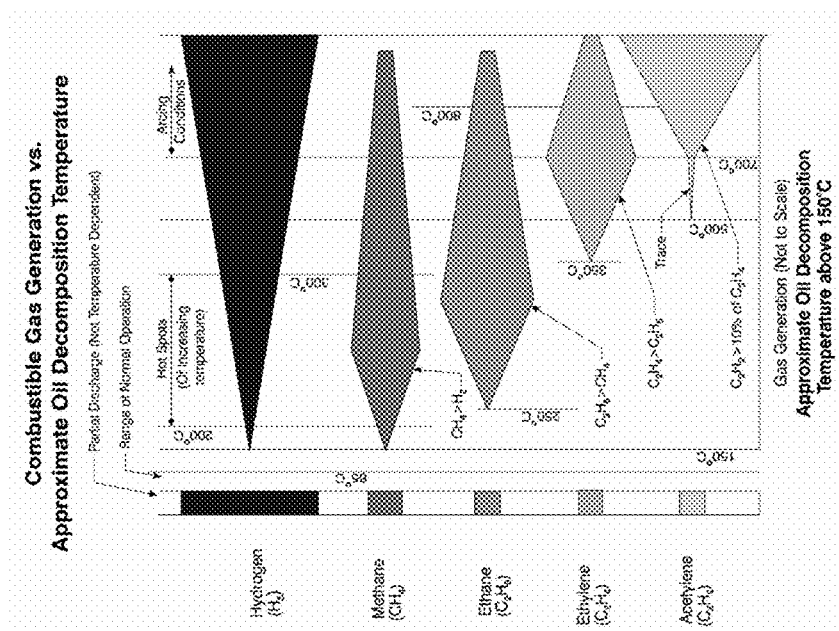
FIG. 7 shows combustible gas generation v. approximate oil decomposition temperature.

Referring to FIG. 7, overstressed insulation in oil filled transformers produces various gasses which are absorbed into the oil. The quantity and composition of these gasses depends partly on the kind of insulation and the temperature. By extracting the gasses from the oil and analyzing them it is possible to diagnose the kind of failure which produced them and where the damage is occurring.

Dissolved gas analysis is the procedure by which the gasses are analyzed. The type of gasses and their concentration in the oil are used to identify problems in a transformer before a failure occurs. This technique can be used to identify problems in any part of a transformer that is in contact with the oil (or allows communication of the gases to components in contact with the oil). The test, however, is not specific for the exact location and cause of the fault.

Different gases are produced by the decomposition of oil at different temperatures. Hydrogen is generated with fairly low energy faults, such as partial discharge, and temperature as low as 150° C. In this temperature range (150° C.-200° C.), methane is also produced. Beginning at approximately 200° C., Ethane is generated. At still higher temperatures in excess of 300° C., Ethylene is produced. Under the highest temperatures, generally associated with arcing conditions, Acetylene is produced. It is important to keep in mind that high energy faults will produce a gradient of temperatures around the fault location, generating the lower-energy fault gases in some quantity. By examining the quantity and type of gases present, it is possible to assess the general type of fault present, and to some degree the magnitude of fault.

DGA operates on the principle that certain gases are generated as oil degrades at certain temperatures or energies. For examples, Ethylene is generally generated at temperatures in excess of 700° C., well above normal transformer operating temperatures. Acetylene ($C_2H_2$) is usually generated only at temperatures that are seen when an arc passes through the oil. It is usually best to begin with the gases that are generated at the highest energies.

High-intensity electrical discharges, or electrical arcs, produce very high temperature (over 600° C. to 700° C.), which causes the generation of small but significant quantities of acetylene. Acetylene is absent for other types of faults, so it is a reason for major concern when it is detected. In a large, high current arc, there will be a distribution of temperatures in the oil around the arc, so we expect to see some levels of the other heating gases. Generally, 5-10 ppm of Acetylene is enough to raise alarm and 35 ppm or higher requires immediate action.

Lower, steadily increasing levels of Acetylene can be produced by small, intermittent sparking seen when circulating currents are interrupted, e.g. core bolt sparking, sparking between core laminations, or from a failing pump motor. Acetylene can also be generated in significant quantities if there is heavy partial discharge taking place.

In the absence of Acetylene, we look next at Ethylene. High Ethylene (above roughly 100 pm) or a significant lasting trend in Ethylene indicates temperatures above 700° C. This means something in the transformer is getting excessively hot. This can be a bad joint, a core problem or occasionally, some broken turns strands. One thing to check is the trend in CO. If CO is trending upwards, this indicates that the heating is located somewhere in contact with paper. $CO/CO_2$ ratio can also be used to assess paper involvement, but this is often less reliable ($CO_2$ often varies quite a bit from sample to sample and is easily introduced by air bubbles in the sample).

Methane and Ethane are the other key heating gases. They are generated at temperatures roughly below 300° C. High levels of these gases can indicate some high localized heating, but may also be indicative of a transformer that is simply heavily loaded.

Again, CO can be utilized to assess paper involvement. Here, levels above 150 ppm raise caution and levels above roughly 250 ppm raise alarm. Also, look for a sharp increase in these levels, as this indicates that something changed. Trend is often more important than level here.

Low-intensity electrical discharges in oil, sometimes referred to as corona, produce principally hydrogen, with some methane, but lesser quantities of the other hydrocarbon gases.

Hydrogen is a tricky gas to interpret. Steadily increasing Hydrogen levels in the absence of any other gases generally indicates some partial discharge activity. However, this is not terribly reliable. There are some cases that are clear examples of Hydrogen produced by partial discharge, with Hydrogen in the hundreds and low levels of other gases.

There are some other potential, though rare, sources for Hydrogen generation in the absence of heating gases. Hydrogen can occasionally be generated by oxidation of the tank steel if there is free water present. Some also claim the "thin film" heating of oil in between core laminations can generate hydrogen at core temperatures in excess of 120° C.

Carbon monoxide and carbon dioxide (CO and $CO_2$). CO and $CO_2$ are the key gases produced by thermal degradation of the paper, and are often used as indicators of paper involvement in a fault. Thermal decomposition of cellulose, even at normal operating temperatures, produces these carbon oxide gases. Thus, low rates of production are not a cause for alarm. However, production of such gases at an abnormally high rate is associated with overheated insulation. Both the rate of production and the ratio of the two gases can be indicative of the severity of the overheating.

If a fault involves the cellulose insulation, or is near enough to cellulose insulation to sufficiently heat the paper, degradation of the paper will occur via hydrolysis, oxidation or pyrolysis. If the fault is a low temperature thermal fault (<150° C.), then hydrolysis and oxidation will be the dominant mechanisms. This is consistent with thermal aging due to normal operation. However, above roughly 150° C., pyrolysis becomes more dominant, producing more CO. As a general rule of thumb, the $CO_2/CO$ ratio should be between 3 and 10. Outside of this range, excessive degradation of the cellulose is likely. Ratios closer to 1, with higher rates of CO generation, are indicative of pyrolysis and, therefore, excessive temperatures. Examples of extreme overheating from loss of cooling have produced ratios in the 2-3 range. (This ratio should be based on relative ppm of gas generated in a given time period, rather than total gas content, to more accurately assess the latest temperature condition.)

Caution must be exercised when interpreting CO and $CO_2$ values and the ratio of $CO_2/CO$. $CO_2$ results can easily be skewed by the exposure to air, either within the transformer or by accidentally drawing an air bubble with the sample. This would skew the ratio toward higher numbers. In addition, CO and $CO_2$ can be generated from other sources, such as degradation of paints, coatings, adhesives and the oil, albeit in lower quantities.

As an example, a transformer with $CO_2$ level at 12000 ppm and CO at 870 ppm had the diagnosis of imminent risk of failure confirmed by teardown when grossly overheated insulation was found at the line end of the HV winding due to a manufacturing defect which restricted cooling in a limited area.

Note that in this example the $CO_2/CO$ ratio was not abnormal, so both criteria should be investigated. An unusually low $CO_2/CO$ ratio with small amounts of gas present could be indicative of a developing problem that could be corrected. The absolute quantities of gas should at least be in the Condition 2 status before any detailed investigation was undertaken.

Investigation would include frequent measurement of gas-in-oil to establish the generation rate. Since all normally operating transformers will have some levels of the above mentioned gases dissolved in the oils (generally with the exception of acetylene), it is not a simple task to identify a definitive threshold for each gas. There are two general tasks in DGA analysis: 1) fault detection and 2) fault classification. Obviously, if there is no fault present, then there is no fault to classify. Many artificial intelligence applications in transformer DGA have focused on fault classification. This isn't terribly useful, since the most difficult determination to make is whether or not a fault is present to begin with.

Unfortunately, there are no simple rules or thresholds that can be given for precisely and definitively determining the presence of a fault. There is a great deal of uncertainty that makes the process more "art" than science. Part of the difficulty lies in the interrelationship of the various gases. Thresholds for concern are often expressed as limits on the individual gases without regard for the levels of other gases. This is can be a misleading approach, however.

While a certain gas level might be concerning in the absence of other gases, in conjunction with other gases this same gas level might indicate a less concerning condition. For example, generation of Hydrogen alone might indicate partial discharge activity, a serious condition. However, in conjunction with some of the heating gasses (Methane, Ethane), the same Hydrogen levels might indicate a heavily loaded unit.

Knowledge of the transformer design and its history in service is also very important in the interpretation process. For example, certain Westinghouse shell form transformers had a stray flux heating problem with the tee-beam that supports the windings. These units will generate excessive quantities of the heating gases (Methane, Ethane and Ethylene) and even some Acetylene. Without taking into consideration this particular design issue, these gas levels would be highly alarming. However, experience has shown that these units can continue to operate while generating these high levels of gases.

In other cases, similar patterns of gassing could be indicators of evolving incipient faults in the windings, such as the evolution from a small strand-to-strand fault into a disastrous turn-to-turn or section-to-section fault. This type of knowledge, combined with the gas-in-oil history, is essential in the decision-making process for deciding the appropriate course of action once a potential problem has been identified. Therefore, a successful DGA interpretation algorithm must include the flexibility to specify knowledge specific to manufacturers, vintages or any other unique category of transformers. See FIG. 6.

It is important to remember that DGA is not a "specific" test. DGA will generally not point to specific failure mechanism, but rather only generally describe the energy involved and perhaps whether the paper insulation is involved. Therefore, the algorithms and knowledge base will be structured to classify faults only to the extent that DGA analysis is capable of discerning between categories of faults. This fault classification can then be combined with other information, such as oil quality, nameplate data or electrical test data to attempt to ascertain a more specific failure mechanism. By structuring the knowledge base in this fashion, the number of rules can be reduce, but more importantly it is assured that the diagnostic value of DGA is not overstated and that any differentiation between failure mechanisms is warranted by the evidence and not an artifact of the knowledge implementation.

Figure 4:
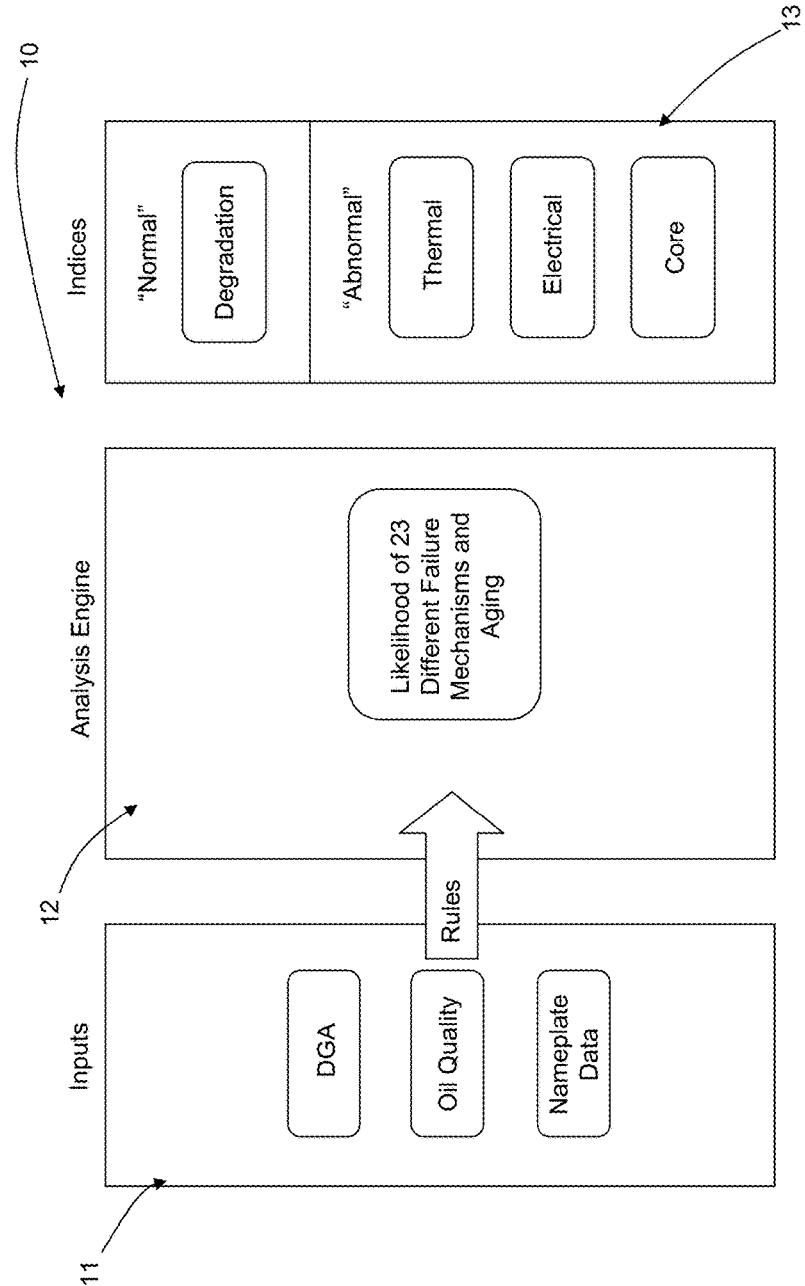
Figure 5:
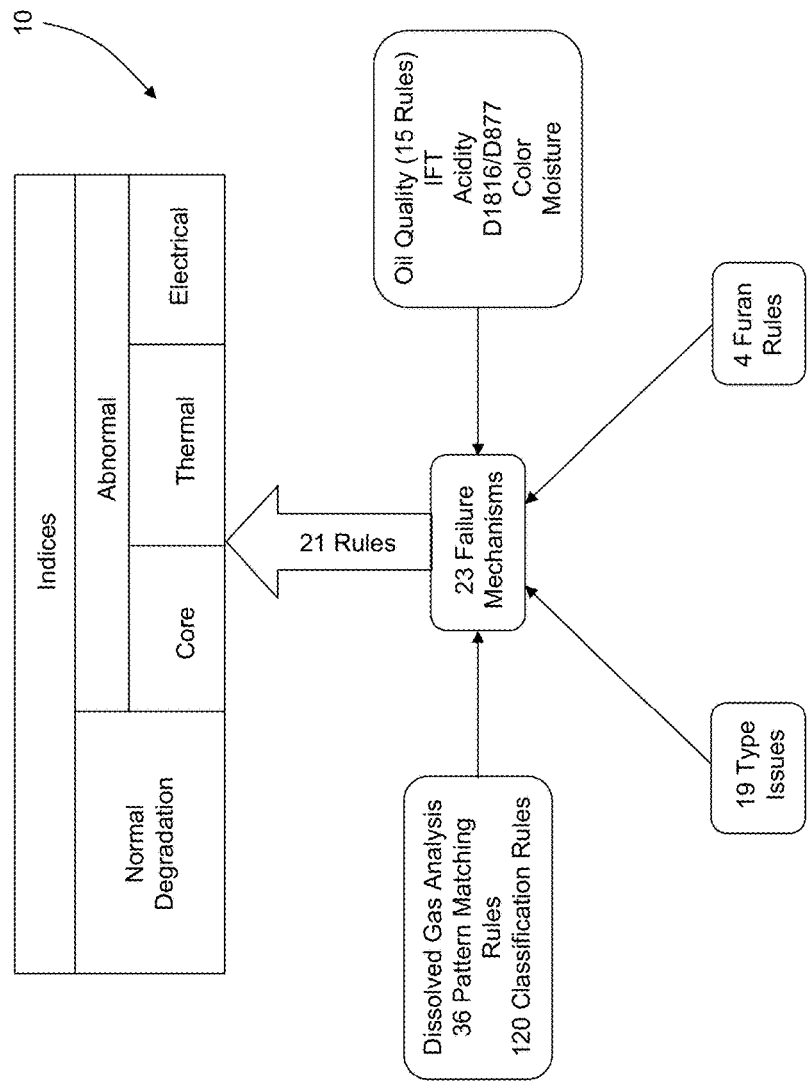
Figure 6:
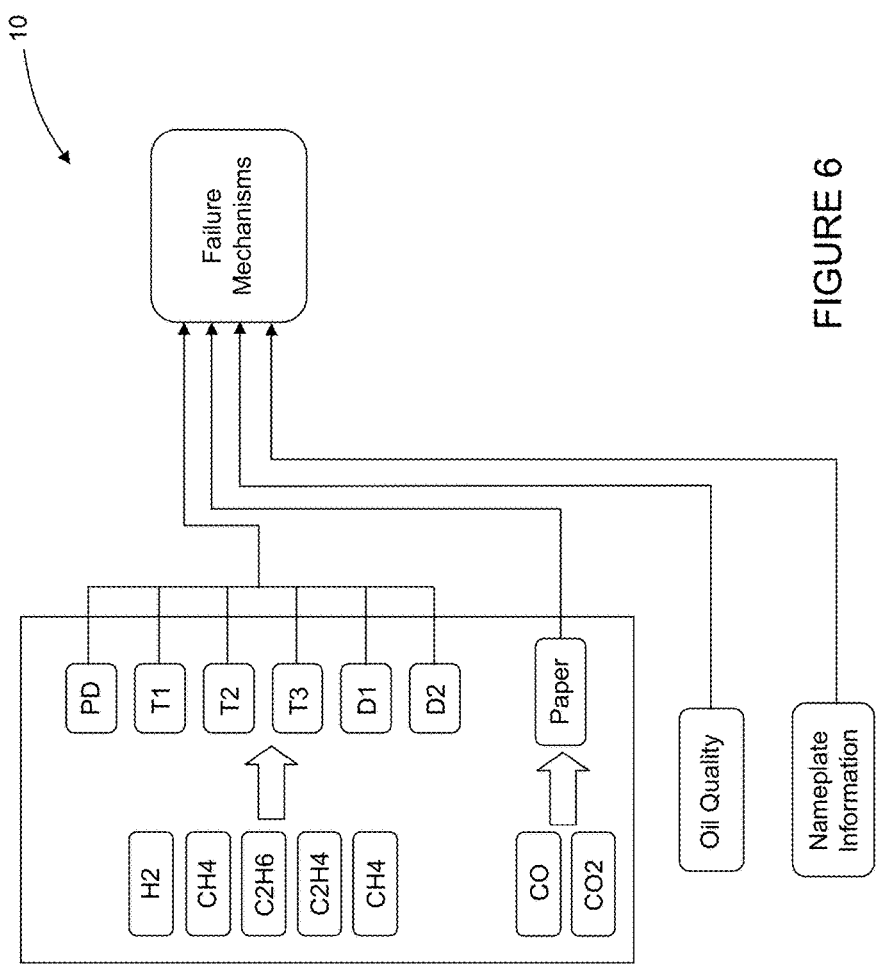

Referring to FIGS. 4 and 5, below is a list of general fault types capable of being discerned by DGA. This reflects a reasonable level of granularity. The rules in the analysis engine will be structured to indicate the presence of faults in these categories. Additional information will then be utilized to differentiate between possible failure mechanisms. Examples of failure mechanisms associated with each fault classification are listed below, as well. These lists are by no means exhaustive.

PD—Partial Discharge: Characterized by generation of Hydrogen, with low levels of Methane and traces of Ethane and Ethylene. May produce CO and $CO_2$ if cellulose insulation is involved. Severe partial discharge can generate Acetylene.

Voids in insulation due to improper impregnation
Contamination from moisture
Contamination from particulates
D1—Low-level Arcing: Characterized by generation of Acetylene, with low levels of Ethylene and other "heating" gases.

Tracking due to contamination or improper design
Insulation puncture or flashover with little power follow through.
Loose core ground
Intermittent unintended core ground
Strand-to-strand fault
D2—High-Level Arcing
Insulation flashover with power follow through.
Due to a variety of causes including poor design, overvoltage, short-circuit damage, contamination.
T1—Temperatures <300° C.
Normal aging
Planned overloading
Stray Flux Heating (Tank, Support Structure)
Circulating currents in core due to multiple core grounds
Winding circulating currents
Bad Joint
Coked contacts
Blocked oil ducts
Clogged coolers
Blocked radiator
Lead Heating
T2—Temperatures >300° C., <700° C.
Stray Flux Heating
Bad Joint, accelerating to failure
Coked contacts
T3—Temperatures >700° C.
Severe Stray Flux Heating
Bad Joint—Critical
Bad De-Energized Tap Changer Contact Trends in gases are commonly overlooked in DGA analysis methodologies. The trends in the gas levels are often more enlightening than the absolute gas levels. The trend can provide some indication of the severity of the fault and whether the fault is active. However, trends pose a great deal of difficulty in formulating automated analytical tools. There is a significant amount of variability in the gas levels, some more so than others. For example, Hydrogen and Methane are particularly variable gases, while the more soluble gases like Ethylene or Acetylene tend to be more stable from one sample to the next. Given the infrequent sampling intervals, there are few data points available to establish a clear trend.

The utility in examining the trends is indisputable. However, discerning between trends due to active gassing and trends that are simply due to analytical error or changes in gas solubility is difficult, even for a trained observer.

The system and method produces indices designed to provide a indication of a transformer's condition in respect to a defined set of internal failure mechanisms. Transformers can fail in innumerable ways. Failure mechanisms are a rough classification of a condition or defect that may result in failure of the transformer. Failure mechanisms, as set forth here, roughly group specific failure scenarios into categories that have similar root causes, fault evolution characteristics and incremental operating risk. Presently, there are 23 different failure mechanisms that have been defined. They are:

Moisture Ingress
Particle Contamination
Oxygen Ingress
Active Thermal Degradation
Winding Local Overheating—Bad Joints
Winding Local Overheating—Eddy Losses
Winding Local Overheating—Circulating Currents
Winding Local Overheating—Magnetic Saturation
Lead Heating
Winding—Mechanical Damage
Winding—Tracking/PD
Winding—Shorted Turn Strands
Winding—Dielectric Failure
Ungrounded Metallic Part
Unintended Core Ground
Core Bolt Insulation Shorting (specific types)
Loose Core Laminations
Core Shorts—Edge Burrs
Core Heating—Overexcitation
Core Heating—Circulating Currents
Core Heating—Unbalanced Flux
Core Heating—DC in Neutral
Core Face Overheating It is natural for subject matter experts to express "beliefs" or the degree to which a given piece of evidence confirms or disconfirms a hypothesis or conclusion. Beliefs allows for quantification of the subjective opinions of subject matter experts and consequently, the indices can be considered as measures of the belief in a particular condition.

Evidence, in the form of test data and nameplate information, is evaluated to determine a "belief" that a given failure mechanism is likely. The belief factors allow for reasoning under the uncertainty that often accompanies substation equipment assessments.

Given sparse information, it is often not possible to specifically pinpoint a single failure mechanism or differentiate between multiple failure mechanisms. Quite often, several potential failure mechanisms are identified concurrently.

As stated above, there are 23 different failure mechanisms, each with it's own belief. If each of the failure mechanisms were examined as the high level output, there would be 23 numbers for each transformer. To summarize the output in a meaningful, yet succinct fashion, four indices were developed. These indices aggregate the beliefs based on the broad physical mode of the individual failure mechanism. The value of these highest level indices is meant to provide a measure of the belief that one or more of the constituent failure mechanisms exists. These indices are comprised of normal degradation and abnormal condition components. The development of normal degradation index to assist with transformer replacement decisions is unique to this development and a major breakthrough.

For example a measure of 1.0 in the Abnormal Core index indicates a high measure of belief that a core failure mechanism exists. Correspondingly, a measure of 0 in the Abnormal Core index would indicate with a high belief that a core failure mechanism does not exist.

Normal Degradation Index

This index is intended to provide an indication of the physical condition of the paper insulating system relative to its initial state. Transformers undergo normal aging or degradation due to operation of the transformer under conditions that do not exceed the design criteria of the transformer. This normal degradation is generally due to aging of the paper insulation system, in which the paper insulation experiences decreasing mechanical strength as a function of time and temperature.

Paper ages at any temperature, however the aging rate is greatly increased as temperature increases. Paper degradation can occur due to hydrolysis, oxidation or pyrolysis, whereby heat, moisture and oxygen are the primary catalysts. These processes break bonds in the cellulose chains, decreasing mechanical strength. Normal degradation is generally a slow process.

Units that have elevated Normal Degradation Indices are not expected to experience a rapid deterioration in condition in the near term. A high normal aging index does not necessarily mean that the transformer is close to failure but rather that it should be a more likely candidate for retirement considerations going forward. This index is primarily useful for fleet and asset management, budgeting and replacement planning. Currently, a Normal Degradation Index of greater than 0.25 indicates a unit that warrants further scrutiny. Experience indicates that Normal Degradation Index values above 0.60 highly correlate with units that have insulating paper that is no longer capable of providing reliable service.

With the minimum amount of information, DGA and vintage, there are limitations to assessing the condition of the paper. Certain gas patterns (high methane, little to no ethylene) suggest a heavily loaded, but normally operating transformer. CO levels and trends are also highly suggestive of degradation, as CO is only generated in a transformer by decomposition of the cellulose chains in the insulating paper. This information combines to generate a belief in whether the recent history indicates that there was active thermal degradation for the preceding time period.

The normal degradation index is calculated is as follows:
1. A belief in "active thermal degradation" is calculated at each point in time based upon available evidence (strictly gases at this step).
2. The belief at each point in time is multiplied by the time interval between the present sample and the previous sample and added to a running sum (simple integration of the "active thermal degradation" over time)
3. This integrated belief is divided by the number of days in the gas history to give an average increment per day.
4. The average increment is multiplied by the number of days in service to give a number representative of the total aging projected over the in-service history of the transformer. Obviously, a lengthy service history will minimize the length of the projection, while providing a greater wealth of history to form a better average rate of degradation.
5. To derive an index from this equivalent age indicator, total aging indicator is normalized over an average life expectancy of 30 years. The magnitude of this average life expectancy is not critical, as thresholds for action are derived through field experience and measurement of degree of polymerization.

Abnormal Thermal, Electrical and Core Indices

This index is used to identify units that may be experiencing a variety of unexpected problems due to manufacturing or operating issues or defects. Transformers in these categories show the existence of some condition that would not be present or expected in normal operation. This could be excessive temperatures that don't fit the pattern of gas seen with normally operating, heavily loaded transformers, or it could be some indication of partial discharge, arcing or sparking. Units with heating gases and no indication of paper involvement may also show up in the "abnormal core" category. The important difference, however, is that this index is NOT a function of service age.

While some vintage-specific type issues may be involved, age does not increase or decrease an abnormal index. These conditions can occur at any point during the service life of a transformer. A high abnormal index value indicates a need to take more immediate action e.g. additional tests or monitoring or inspection. This index indicates transformers that may or may not evolve to failure in the near future. Time to failure is highly variable and dependent on the specifics of any potential underlying fault condition. Higher Abnormal Condition Indices identify transformers that should be reviewed in further detail by appropriate personnel.

Abnormal Condition Indices are divided into three categories: Thermal, Electrical, and Core. Note that due to the non-specific nature of field diagnostic tests, a single defect may provide indications in more than one category. Any Abnormal Condition Index Value above 0.5 warrants further review.

The following is a list of failure mechanisms that contribute to each of the three Abnormal Condition Indices:
Abnormal Thermal
 Contributors:
  Winding Local Overheating—Bad Joints
  Winding Local Overheating—Eddy Losses
  Winding Local Overheating—Circulating Currents
  Winding Local Overheating—Magnetic Saturation
  Lead Heating
Abnormal Electrical
 Contributors:
  Winding—Shorted Turn Strands
  Winding—Dielectric Failure
  Winding—Tracking/PD
  Ungrounded Metallic Part
  Static Electrification
Abnormal Core
 Contributors:
 Unintended Core Grounds
  Ungrounded Metallic Part
  Core Bolt Insulation Shorting
  Loose Core Laminations
  Core Overexcitation
  Core Circulating Currents
  Core Face Heating
  Core Heating—Unbalanced Flux
  Core Shorts—Edge Burrs
  Core Heating—DC in Neutral In addition to the four indices above, an oil quality index has been incorporated into the system. The oil quality in transformers is important for the following reasons:
 Maintaining the dielectric strength of the oil in EHV and UHV transformers has long been recognized as critical. This is intuitive.
 The importance of this is increasing as design margins are reduced to nil.
 Newer research has highlighted the role of moisture, oxygen and acidity of the oil in reducing the longevity of the paper insulation system.
 Deposition of polar contaminants on insulation surfaces is a concern with heavily degraded oil The oil quality index is used in conjunction with the four previously described inidices to provide a more complete picture of transformer health. The system and method allows thresholds, which do not have crisp parameters, to be used. While the thresholds are an important starting place, data tables do not recognize the relative importance of some tests over others. For example, why use one set of thresholds over another set. The following rules can apply in the oil quality index.

If dielectric strength is bad, action must be taken

If IFT is low, action can wait depending on how low it is and the voltage class of the transformer If several parameters are out of bounds, problem is greater and time to action is less More Than Just an Index Oil contamination and degradation can take a variety Oil remediation presents a series of possible corrective actions based on which oil quality parameters are insufficient.

Presenting a single index value, while useful as a gauge for the severity of an oil quality problem within a transformer and across a fleet does not suggest the appropriate remedy A more complex tree of "Actions" must be developed to give the user specific guidance:

Do nothing

Process with vacuum degasser, moisture removal and paper filter

Treatment with Fuller's Earth

Replace the oil

Figure 9:
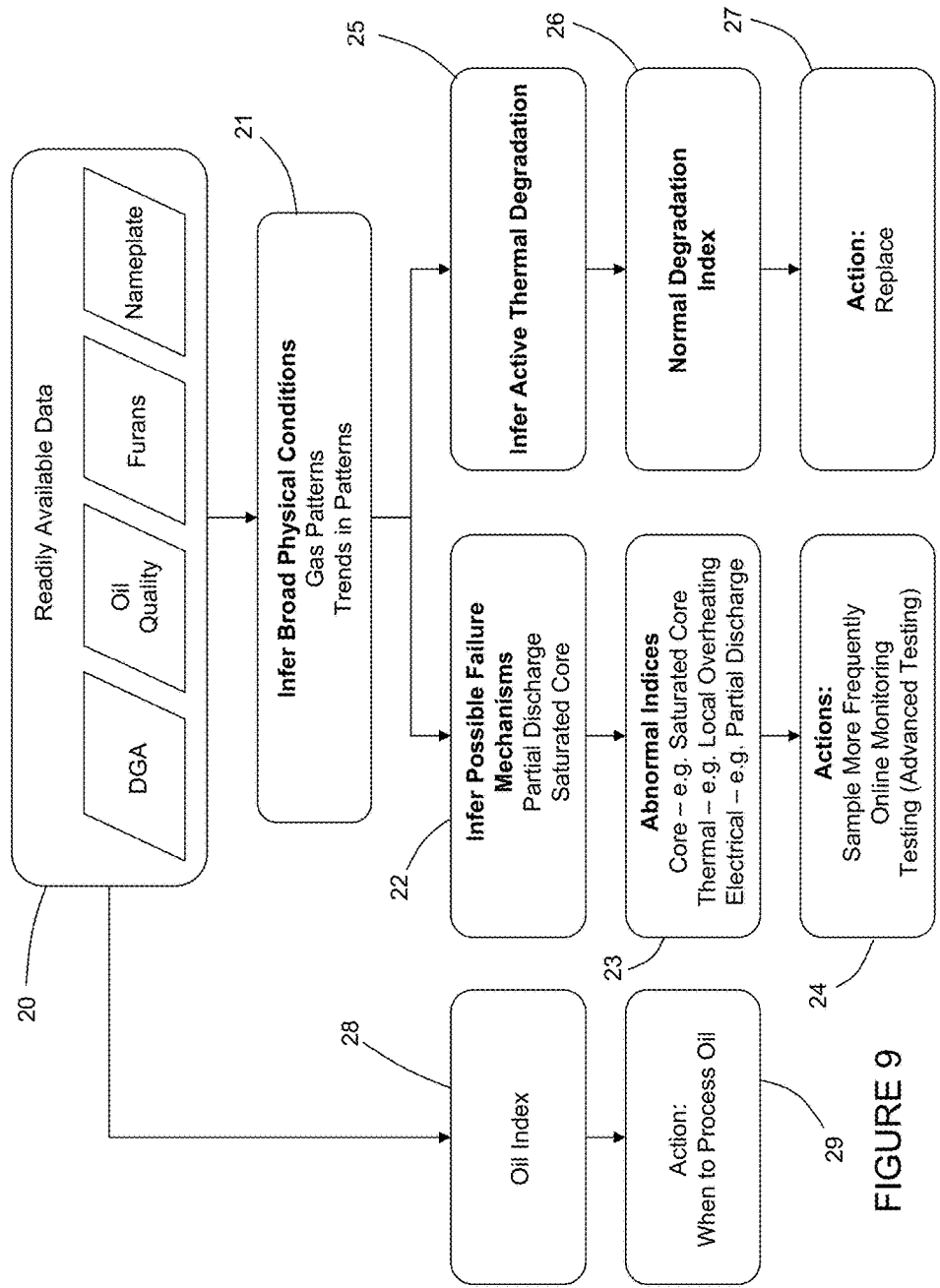
FIG. 9 is a flow chart of the method for evaluating a transformer.

The method for evaluating a transformer is described generally below. The method allows a user to evaluate specific transformers based on data gathered and the rules-based system to determine what type of action should be performed. As shown in FIG. 9, a user first gathers readily available data for inputting into the input module 11 of the system 10 (block 20). The intent of the system and method is to make use of data that is readily available, i.e., obtainable with a minimal amount of effort. For power transformers, this data includes:

Nameplate data (manufacturer, vintage, etc.)

Dissolved Gas Analysis History (DGA), specifically $H_2$, $CH_4$, $C_2H_6$, $C_2H_4$, $C_2H_2$, CO, $CO_2$, $O_2$ and $N_2$ taken at several dates Oil Quality History (Interfacial Tension, Acidity, Dielectric Breakdown Voltage, Moisture and Color)

Furans (2-Furfuraldehyde)

Once the data has been inputted into the input module 11, data from the input module 11 is accessed by the analysis engine module 12. The analysis engine module 12 uses rules to analyze the data. First, the analysis engine module 12 infers broad physical conditions from the data (block 21). More particularly, the data, especially the oil test data (DGA and oil quality) provides indications of broad physical conditions that might occur in the bulk of the transformer oil. These conditions include:

PD—Partial Discharge: Characterized by generation of Hydrogen, with low levels of Methane and traces of Ethane and Ethylene. May produce CO and CO2 if cellulose insulation is involved. Severe partial discharge can generate Acetylene.

Example Rule:    IF Transformer.DGA.blfH2_High AND NOT
(Transformer.DGA.blfCH4_High OR Transformer.DGA.blfC2H6_High
OR
Transformer.DGA.blfC2H4_High OR Transformer.DGA.blfC2H2_High)
THEN
Transformer.DGA.blfLightPD (1.0) ELSE !Transformer.DGA.blfLightPD
(1.0)
END D1—Low-level Arcing: Characterized by generation of Acetylene, with low levels of Ethylene and other "heating" gases (Ethane, Methane).

Example Rule:    IF Transformer.DGA.blfC2H2_High AND NOT
(Transformer.DGA.blfCH4_High OR Transformer.DGA.blfC2H6_High
OR
Transformer.DGA.blfC2H4_High) THEN Transformer.DGA.blfSparking
(1.0)
ELSE !Transformer.DGA.blfSparking (1.0) END D2—High-Level Arcing: Characterized by generation of Acetylene with higher levels of Ethylene and other "heating" gases.

Example Rule: IF Transformer.DGA.blfC2H2_High AND
(Transformer.DGA.blfCH4_High OR Transformer.DGA.blfC2H6_High
OR
Transformer.DGA.blfC2H4_High) THEN Transformer.DGA.blfArcing
(1.0)
ELSE !Transformer.DGA.blfArcing (1.0) END T1—Temperatures <300° C.: Characterized by generation of mostly methane with low levels of Ethane and at most traces of Ethylene. No Acetylene.

Example Rule: IF (Transformer.DGA.blfCH4_Moderate OR
Transformer.DGA.blfC2H6_Moderate) AND NOT
(Transformer.DGA.blfC2H4_High OR
Transformer.DGA.blfC2H2_High) THEN
Transformer.DGA.blfLowHeat (1.0) ELSE
!Transformer.DGA.blfLowHeat (1.0)
END T2—Temperatures >300° C., <700° C.: Characterized by generation of Methane and Ethane with potential of low amounts of Ethylene. No Acetylene.

Example Rule: IF Transformer.DGA.blfCH4_High AND NOT
(Transformer.DGA.blfC2H4_High OR
Transformer.DGA.blfC2H2_High) THEN
Transformer.DGA.blfModerateHeat (1.0) ELSE
!Transformer.DGA.blfModerateHeat (1.0) END T3—Temperatures >700° C.: High amounts of Ethylene with other "heating gases". No Acetylene.

Example Rule: IF Transformer.DGA.blfC2H4_High AND NOT
Transformer.DGA.blfC2H2_VeryHigh THEN
Transformer.DGA.blfHighHeat
(1.0) ELSE !Transformer.DGA.blfHighHeat (1.0) END In addition to the conditions listed above, an assessment of paper involvement from CO, $CO_2$ and $CO_2$/CO ratio (and trends thereof) is performed. Increasing amounts of CO indicate the potential of active degradation of the paper insulation and can help localize the fault to the current carrying circuit. As a general rule of thumb, the $CO_2$/CO ratio should be between 3 and 10. Outside of this range, excessive degradation of the cellulose is likely. Ratios closer to 1, with higher rates of CO generation, are indicative of pyrolysis and, therefore, excessive temperatures.

With the broad physical conditions and the assessment of paper involvement complete (block 21), the analysis engine module 12 takes one of two tracks. The first track is to determine abnormal indices (block 23) and the second track is to determine a normal degradation index (block 26). With respect to the first track, beliefs are assigned or calculated to individual failure mechanisms based on the broad physical conditions and paper involvement (block 22). It is these failure mechanisms that drive the abnormal indices in block 23. For example, belief in Winding Bad Joints is calculated from the following rules:

```
IF Transformer.DGA.blfHighHeatPaper THEN
Transformer.fmWdgBadJoints
(0.6) END
IF Transformer.DGA.blfHighHeatPaperTrend THEN
Transformer.fmWdgBadJoints (0.8) END
IF Transformer.DGA.blfHighHeatNoPaper THEN
Transformer.fmWdgBadJoints (0.6) END
IF Transformer.DGA.blfHighHeatNoPaperTrend THEN
Transformer.fmWdgBadJoints (0.8) END
IF Transformer.DGA.blfArcing THEN Transformer.fmWdgBadJoints
(0.1) END
IF Transformer.DGA.blfArcingTrend THEN
Transformer.fmWdgBadJoints
(0.2) ELSE !Transformer.fmWdgBadJoints (0.1) END
IF Transformer.DGA.blfSparking THEN Transformer.fmWdgBadJoints
(0.4)
END
IF Transformer.DGA.blfSparkingTrend THEN
Transformer.fmWdgBadJoints
(0.6) END
```

For each abnormal index, a pre-determined set of failure mechanisms is used to calculate the indices as a maximum belief in. The pre-determined failure mechanisms are listed below by index.

Abnormal Thermal Index:
   Winding Local Overheating—Bad Joints
   Winding Local Overheating—Eddy Losses
   Winding Local Overheating—Circulating Currents
   Winding Local Overheating—Magnetic Saturation
   Lead Heating Abnormal Electrical Index:
   Winding—Shorted Turn Strands
   Winding—Dielectric Failure
   Winding—Tracking/PD
   Ungrounded Metallic Part
   Static Electrification Abnormal Core Index:
   Unintended Core Grounds
   Ungrounded Metallic Part
   Core Bolt Insulation Shorting
   Loose Core Laminations
   Core Overexcitation
   Core Circulating Currents
   Core Face Heating
   Core Heating—Unbalanced Flux
   Core Shorts—Edge Burrs
   Core Heating—DC in Neutral With the beliefs for the failure mechanisms in each index determined using the process described above, the maximum belief calculated for the group is used to determine the abnormal index. For example, if "Bad Joints" is the highest calculated belief for the abnormal thermal index, then the abnormal thermal index is equal to that belief. With the abnormal indices determined, the output module 13 outputs the results for the user to review. If any of the Abnormal Indices (Thermal, Electrical, or Core) exceeds 0.5, then an investigation for potential incipient fault is needed and corrective action is taken if necessary (block 24). Example actions include (1) changing oil sampling frequency, (2) installing online monitoring, (3) electrical testing, and (4) performing an outage and conducting internal inspections.

For track two, the broad physical conditions and the paper involvement are used to calculate beliefs in active thermal degradation (block 25). An example rule is as follows:

```
IF Transformer.DGA.blfPaperTrend THEN
Transformer.fmActiveThermalDegradation (0.90) ELSE
!Transformer.fmActiveThermalDegradation (0.90) END
```

Once the active thermal degradation belief is determined, the normal degradation index is calculated (block 26) using the following steps:

Multiply belief in active thermal degradation by the time interval between the present test date and the previous test date and add to a running sum (Integrated Normal Degradation Increment). All of the above described steps are repeated for each test point in history, chronologically ordered.

The Integrated Normal Degradation Increment is divided by the number of days in the test history to give an average increment per day.

The average increment is multiplied by the number of days in service to give a number representative of the total aging projected over the in-service history of the transformer. Obviously, a lengthy service history will minimize the length of the projection, while providing a greater wealth of history to form a better average rate of degradation.

The Normal Degradation Index is then determined by normalizing the total ageing indicator over an average life expectancy of 30 years. The magnitude of this average life expectancy is not critical, as thresholds for action are derived through field experience and measurement of degree of polymerization.

The output module 13 provides a user with the calculated normal degradation index. If the normal degradation index is greater than 0.25 then an indication of potential degradation exists and further investigation for replacement is warranted. At this point, furan analysis would be performed, as well as any additional offline analysis to support or prioritize replacement decisions (block 27).

Figure 10:
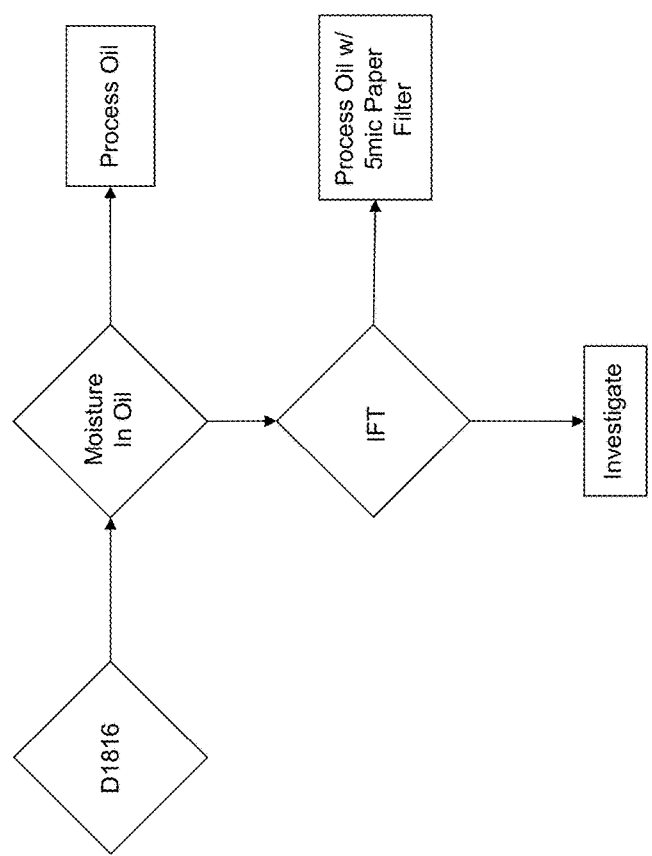
FIGS. 10 and 11 show flow charts for oil and end of life evaluation.
Figure 11:
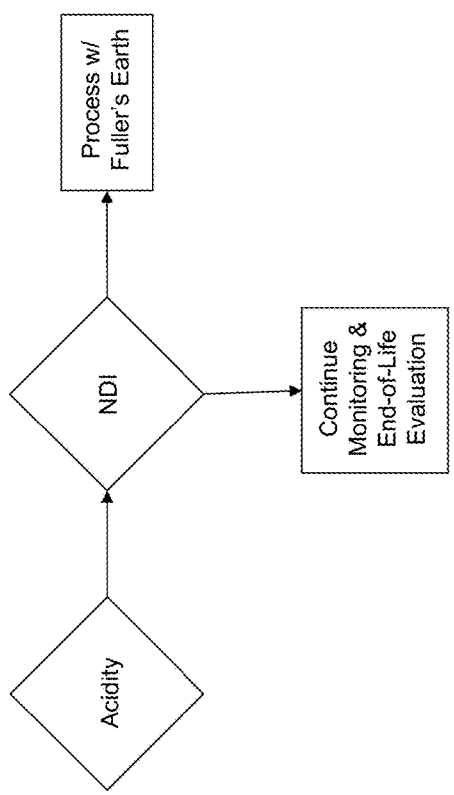

In addition to the first and second tracks, an oil index (block 28) is determined from the readily available data (block 20). The oil index is used to determine when to process the oil in a transformer (block 29). See FIGS. 10 and 11. The following example rules are used by the analysis engine module 12 to calculate the oil index from oil quality test data:

```
Example Rules: IF Transformer.Description.HV_kV >= 230 AND
Transformer.OilQuality.Acidity == HIGH(0.08, 0.12)
THEN
Transformer.OilQuality.blfHighAcidity(1.0) END
IF Transformer.Description.HV_kV >= 230 AND
Transformer.OilQuality.Acidity == LOW(0.08, 0.12) THEN
!Transformer.OilQuality.blfHighAcidity(1.0) END
IF Transformer.OilQuality.blfLowDielectric_D1816_1mm THEN
Transformer.fmOilDegradation (0.9) ELSE
!Transformer.fmOilDegradation
(0.7) END
```

With the oil index calculated, an action by a user is determined (process oil, process oil with 5mic paper filter, process oil with Fuller's Earth, investigate, and continue monitoring). An example rule includes:

```
IF Transformer.DGA.blfC2H2_Trend_High THEN
Transformer.actionWeeklyOilSampling(1.0) END
```

Analysis of various transformers was performed using the above described system and method. The results are shown below.

EXAMPLES

Example 1

345/118/34.5 kV 672MVA FOA 1995 North American Transformer
Dislodged magnetic shunts
Repaired on site Oct. 26, 2007
Date of last oil sample used in analysis: Oct. 25, 2007
Normal Degradation Index=0.09
Abnormal Thermal Index=0.28
Abnormal Electrical Index=0.92
Abnormal Core Index=0.46
Flagged Abnormal by System

Example 2

345/230/13.2 kV 336/448/560MVA FOA 1991 ABB
Inadequate core cooling, shifted laminations
Removed from service late 2007. Rewound 2008.
Date of last oil sample used in analysis: Aug. 20, 2007
Normal Degradation Index=0.73
Abnormal Thermal Index=0.57
Abnormal Electrical Index=0.72
Abnormal Core=0.46
Flagged Abnormal by System

Example 3

112.8/14 kV 62.5MVA FOA 1952 General Electric
Failed Sep. 7, 2012. No additional information given.
Date of last oil sample used in analysis: Dec. 2, 2010
Normal Degradation Index=0.63
Abnormal Thermal Index=0.10
Abnormal Electrical Index=0.00
Abnormal Core Index=0.00
NOT flagged abnormal by System
No anomalous test data prior to failure
Last DGA sample 2 years prior to failure

Example 4

115/13.8 kV 25MVA FOA 1977 McGraw Edison
Failed Nov. 14, 2003. Lead failure during throughfault.
Date of last oil sample used in analysis: Oct. 10, 2003
Normal Degradation Index=0.33
Abnormal Thermal Index=0.07
Abnormal Electrical Index=0.07
Abnormal Core Index=0.00
NOT Flagged abnormal by System
High trend in H2 between March 2003 & July 2003. This pattern is not uncommon, as H2 tends to be easily produced.
It appears that the failed lead was in a weakened state and failed while carrying fault current.

Example 5

S/N 90198-A 345/118/34.5 kV 672MVA FOA 1995 North American Transformer
Dislodged magnetic shunts
Repaired on site Oct. 26, 2007
Date of last oil sample used in analysis: Oct. 25, 2007
Normal Degradation Index=0.09
Abnormal Thermal Index=0.28
Abnormal Electrical Index=0.92
Abnormal Core Index=0.46
Flagged Abnormal by System

Example 6

S/N AEM30712 345/230/13.2 kV 336/448/560MVA FOA 1991 ABB
Inadequate core cooling, shifted laminations
Removed from service late 2007. Rewound 2008.
Date of last oil sample used in analysis: Aug. 20, 2007
Normal Degradation Index=0.73
Abnormal Thermal Index=0.57
Abnormal Electrical Index=0.72
Abnormal Core=0.46
Flagged Abnormal by System

Example 7

S/N 02-8226-52761-1 110/14.4 kV 56MVA FOA 1971 Allis Chalmers
Failed during throughfault on Jun. 7, 2010
Date of last oil sample used in analysis: Mar. 16, 2010
Normal Degradation Index=0.65
Abnormal Thermal Index=0.32
Abnormal Electrical Index=0.05
Abnormal Core Index=0.15
NOT flagged abnormal by System
No anomalous test data prior to failure
Given that it was a throughfault failure, do not expect prior indications. However, the high NDI suggests advanced paper degradation, elevating risk of failure on throughfault.

Example 8

S/N 8975515 112.8/14 kV 62.5MVA FOA 1952 General Electric
Failed Sep. 7, 2012. No additional information given.
Date of last oil sample used in analysis: Dec. 2, 2010
Normal Degradation Index=0.63
Abnormal Thermal Index=0.10
Abnormal Electrical Index=0.00
Abnormal Core Index=0.00
NOT flagged abnormal by System
No anomalous test data prior to failure
Last DGA sample 2 years prior to failure

Example 9

S/N C179320 116.7/14 kV 62.5MVA FOA 1954 General Electric
Failed Jul. 2, 2012. No additional information given.
Date of last oil sample used in analysis: Jul. 5, 2011
Normal Degradation Index=0.09
Abnormal Thermal Index=0.43
Abnormal Electrical Index=0.56
Abnormal Core Index=0.34
Flagged abnormal by System
Last DGA sample approx. 1 year prior to failure

Example 10

S/N CO562951 115/13.8 kV 25MVA FOA 1977 McGraw Edison
Failed Nov. 14, 2003. Lead failure during throughfault.
Date of last oil sample used in analysis: Oct. 10, 2003
Normal Degradation Index=0.33
Abnormal Thermal Index=0.07
Abnormal Electrical Index=0.07
Abnormal Core Index=0.00
NOT Flagged abnormal by System
High trend in H2 between March 2003 & July 2003. This pattern is not uncommon, as H2 tends to be easily produced.
According to Xcel report: "It appears that the failed lead was in a weakened state and failed while carrying fault current. It is possible that the transformer could have remained in service for quite some time absent a through fault on the X1 winding"

Example 11

S/N M102052 230/115 kV 65MVA FOA 1981 General Electric
Still operating
Date of last oil sample used in analysis: Apr. 2, 2012
Normal Degradation Index=0.25
Abnormal Thermal Index=0.12
Abnormal Electrical Index=0.00
Abnormal Core Index=0.00
Trending low-to-moderate temperature heating gases. Likely a heavily loaded unit, and not due to abnormal condition.

Example 12

S/N 7000257 110/13.8 kV 84?MVA FOW 1964 Westinghouse
Still operating
Date of last oil sample used in analysis: Jan. 13, 2013
Normal Degradation Index=0.24
Abnormal Thermal Index=0.28
Abnormal Electrical Index=0.34
Abnormal Core Index=0.34
DGA is largely unremarkable, with some signs of active paper degradation. Recommend furan sampling.

Example 13

S/N C255508 110/14 kV 62.5MVA FOA 1957 General Electric
Still operating
Date of last oil sample used in analysis: Jan. 15, 2008
Normal Degradation Index=0.00
Abnormal Thermal Index=0.10
Abnormal Electrical Index=0.00
Abnormal Core Index=0.00
DGA is completely unremarkable, with the exception that history ends in 2008

The foregoing has described a system and method for assessing a power transformers. While specific embodiments of the present invention have been described, it will be apparent to those skilled in the art that various modifications thereto can be made without departing from the spirit and scope of the invention. Accordingly, the foregoing description of the preferred embodiment of the invention and the best mode for practicing the invention are provided for the purpose of illustration only and not for the purpose of limitation.

We claim:

1. A method of maintaining a power transmission system of the type including a plurality of interconnected power transformers, comprising the steps of:
(a) acquiring data representing one or more parameters of a power transformer, wherein the step of acquiring data includes the step of acquiring dissolved gas analysis data from a sample of oil contained in the power transformer;
(b) analyzing the acquired data using pre-defined rules to derive one or more broad physical conditions for each of the plurality of power transformers to compute a plurality of indices representing failure mechanisms of the power transformers, wherein the plurality of indices include one or more abnormal indices, a normal degradation index, and an oil quality index;
(c) using the dissolved gas analysis data to compute the normal degradation index for each of the plurality of power transformers;
(d) identifying a subset of the plurality of power transformers having a normal degradation index value greater than 0.60; and
(e) replacing the subset of power transformers.

2. The method according to claim 1, wherein the parameters are selected from the group consisting of nameplate data, dissolved gas analysis history, oil quality history, and furans.

3. The method according to claim 1, wherein the broad physical conditions include partial discharge, low-level arcing, high-level arcing, temperatures less than 300 degrees Celsius, temperatures greater than 300 degrees Celsius and less than 700 degrees Celsius, and temperatures greater than 700 degrees Celsius.

4. The method according to claim 1, wherein the broad physical conditions include assessment of paper involvement.

5. The method according to claim 1, wherein the one or more abnormal indices is selected from the group consisting essentially of abnormal thermal index, abnormal electrical index, and abnormal core index.

6. The method according to claim 1, further including the step of assigning failure mechanisms to each of the one or more abnormal indices and assigning a belief to each of the individual failure mechanisms.

7. The method according to claim 6, further including the step of determining a maximum belief assigned to a failure mechanism for each abnormal index and assigning the maximum belief to that abnormal index.

8. The method according to claim 7, wherein if any of the one or more abnormal indices have a maximum belief greater than 0.5, then an investigation and corrective action is taken.

9. The method according to claim 1, wherein if the normal degradation index is greater than 0.25 then an indication of potential degradation exists and further investigation and replacement action is taken.

10. The method according to claim 8, wherein the corrective action is selected from the group consisting of changing oil sampling frequency, installing online monitoring, electrical testing, and conducting an internal inspection.

11. A system configured to evaluate and diagnose a condition of a power transformer contained in a power transmission system, comprising:

(a) a computing device configured to provide a user interface to allow a user to input data and execute rules to analyze the data; and (b) a plurality of modules executed by the computing device, the modules being configured to conduct various stages of analysis on one or more power transformers, the modules comprising:

(i) an input module executed by the computing device to allow a user to input data gathered for each power transformer being analyzed;

(ii) an analysis engine module executed by the computing device in response to the data being entered into the system, the analysis engine executing pre-defined rules to determine indices, wherein the analysis engine module assigns beliefs to pre-determined power transformer failures and assigns individual failures to a pre-determined index, wherein the pre-determined indices include an abnormal index, a normal degradation index; and an oil quality index; and (iii) an output module executed by the computing device in response to the analysis engine module determining indices, the output module displaying results of the analysis engine module for a user to view and prompting the user to perform an action representative of a value assigned to the indices.

12. The system according to claim 11, wherein each of the beliefs have a value between −1 and +1.

13. The system according to claim 12, wherein the analysis engine module assigns the maximum belief for the power transformer failures contained in a pre-determined index to the pre-determined index and outputs the maximum belief to the output module for viewing by a user.

14. The system according to claim 11, wherein the abnormal index includes an abnormal thermal index, an abnormal electrical index, and an abnormal core index.

15. The system according to claim 14, wherein if a maximum belief assigned to a failure mechanism for each abnormal index is greater than 0.5 then the computing device prompts the user to investigate and take corrective action.

16. The system according to claim 14, wherein if the maximum belief assigned to the normal degradation index is greater than 0.25 then the computing device provides an indication that potential degradation exists and prompts the user to investigate and replace the power transformer.

\* \* \* \* \*